United States Patent
Russell et al.

(10) Patent No.: US 9,620,348 B2
(45) Date of Patent: Apr. 11, 2017

(54) INTEGRATED ELECTROSPRAY IONIZATION EMITTER AND DETECTION CELL FOR PARALLEL MEASUREMENTS BY FLUORESCENCE AND MASS SPECTROMETRY

(71) Applicant: Wisconsin Alumni Research Foundation, Madison, WI (US)

(72) Inventors: Jason Dale Russell, Middleton, WI (US); Joshua Jacques Coon, Middleton, WI (US); Ryan Tyler Hilger, Lafayette, IN (US); Lloyd Michael Smith, Madison, WI (US); Daniel T. Ladror, Madison, WI (US); Michael Robert Shortreed, Portage, WI (US); Mark Andrew Scalf, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 653 days.

(21) Appl. No.: 13/927,650

(22) Filed: Jun. 26, 2013

(65) Prior Publication Data
US 2013/0292581 A1 Nov. 7, 2013

Related U.S. Application Data

(62) Division of application No. 13/037,816, filed on Mar. 1, 2011, now Pat. No. 8,506,803.

(51) Int. Cl.
*H01J 49/00* (2006.01)
*G01N 21/64* (2006.01)
*H01J 49/16* (2006.01)
*G01N 21/00* (2006.01)

(52) U.S. Cl.
CPC ........ *H01J 49/167* (2013.01); *G01N 21/6486* (2013.01)

(58) Field of Classification Search
CPC combination set(s) only.
See application file for complete search history.

(56) References Cited

U.S. PATENT DOCUMENTS

| | | | |
|---|---|---|---|
| 6,444,475 B1 * | 9/2002 | Anderson, Jr. | ........ G01N 30/96 210/188 |
| 6,670,607 B2 | 12/2003 | Wood et al. | |
| 7,186,974 B2 | 3/2007 | Tojo | |
| 7,541,578 B2 | 6/2009 | Weng | |
| 8,299,426 B2 | 10/2012 | Dubey et al. | |
| 2002/0003209 A1 | 1/2002 | Wood et al. | |
| 2004/0156753 A1 | 8/2004 | Roitman et al. | |

(Continued)

OTHER PUBLICATIONS

Ficarro (Anal, Chem. 2009, 81, 3440-3447).

(Continued)

*Primary Examiner* — Krishnan S Menon
*Assistant Examiner* — Ryan B Huang
(74) *Attorney, Agent, or Firm* — Boyle Fredrickson, S.C.

(57) ABSTRACT

An integrated mass spectrometer electrospray emitter and fluorescence detector allows improved volumetric measurements of separate components from a liquid chromatography column by improving correlation between the readings of these instruments and reducing dead volume and sample size requirements.

8 Claims, 3 Drawing Sheets

(56) References Cited

U.S. PATENT DOCUMENTS

| | | | |
|---|---|---|---|
| 2004/0200776 A1* | 10/2004 | Ivanov | B01J 20/26 |
| | | | 210/656 |
| 2006/0264779 A1* | 11/2006 | Kemp | A61B 5/1411 |
| | | | 600/583 |
| 2010/0193683 A1* | 8/2010 | Marto | G01N 30/6004 |
| | | | 250/288 |
| 2011/0290009 A1 | 12/2011 | Karger et al. | |
| 2012/0153143 A1 | 6/2012 | Kennedy et al. | |

OTHER PUBLICATIONS

Swaile, D.F., et al., Laser-Based Fluorometric Detection Schemes for the Analysis of Proteins by Capillary Zone Electrophoresis, Journal of Liquid Chromatography & Related Technologies, 14(5) pp, 869-893, 1991, Taylor & Francis, Abingdon, Oxfordshire, UK.

Chang, Huan-Tsung, et al., On-Column Digestion of Protein for Peptide Mapping by Capillary Zone Electrophoreses with Laser-Induced Native Fluorescence Detection, Anal. Chem., 1993, 65, 2947-2951, American Chemical Society, Washington, DC, USA.

Timperman, Aaron T., et al., Native Fluorescence Detection and Spectral Differentiation of Peptides Containing Tryptophan and Tyrosine in Capillary Electrophoresis, Anal. Chem., 1995, 67, 3421-3426, American Chemical Society, Washington, DC, USA.

Okerberg, Eric, et al., Attomole-Level Protein Fingerprinting Based on Intrinsic Peptide Fluorescence, Analytical Chemistry, 2001, 73, 1610-1613, American Chemical Society, Washington, DC, USA.

Garcia-Campana, Ana M., et al., LIF Detection of Peptides and Proteins in CE, Electrophoresis 2007, 28, pp. 208-232, Wiley-VCH Verlag GmbH & Co. KGaA, Weinheim, Germany.

Lee, Thomas T., et al., High-sensitivity Laser-induced Fluorescence Detection of Native Proteins in Capillary Electrophoresis, Journal of Chromatography; 595 1992, pp. 319-325, Elsevier Science Publishers B.V., Amsterdam, The Netherlands.

Schlabach, Timothy, D., et al., Fluorescent Techniques for the Selective Detection of Chromatographically Separated Peptides, Analytical Biochemistry 127, pp. 222-233, 1982, Academic Press, Elsevier, Amsterdam, The Netherlands.

Heath, Timothy G., et al., Reversed-phase Capillary High-performance Liquid Chromatography with On-line UV, Fluorescence and Electrospray Ionization Mass Spectrometic Detection in the Analysis of Peptides and Proteins, Journal of Chromatography, 638, pp. 9-19, 1993, Elsevier Science Publishers B.V., Amsterdam, The Netherlands.

Lacroix, Marlene, et al., Laser-Induced Fluorescence Detection Schemes for the Analysis of Proteins and Peptides Using Capillary Electrophoresis, Electrophoresis 2005, 26, pp. 2608-2621. Wiley-VCH Verlag GmbH & Co. KGaA, Weinheim, Germany.

Sluszny, Chanan, et al., Light-emitting Diode-induced Fluorescence Detection of Native Proteins in Capillary Electrophoresis, Electrophoresis 2005, 26, pp. 4197-4203, Wiley-VCH Verlag GmbH & Co. KGaA, Weinheim, Germany.

Okerberg, Eric, et al., Neuropeptide Analysis Using Capillary Electrophoresis with Muitiphoton-Excited Intrinsic Fluorescence Detection, Analytical Biochemistry 292, pp. 311-313, 2001, Academic Press, Elsevier, Amsterdam, The Netherlands.

\* cited by examiner

INTEGRATED ELECTROSPRAY IONIZATION EMITTER AND DETECTION CELL FOR PARALLEL MEASUREMENTS BY FLUORESCENCE AND MASS SPECTROMETRY

CROSS REFERENCE TO RELATED APPLICATION

This application is a divisional application of U.S. application Ser. No. 13/037,816 filed Mar. 1, 2011, the disclosure of which is hereby incorporated by reference.

STATEMENT REGARDING FEDERALLY SPONSORED RESEARCH OR DEVELOPMENT

This invention was made with government support under HV028182, HG004952, GM080148, and GM081629 awarded by the National Institutes of Health, and 0809095 awarded by the National Science Foundation. The government has certain rights in the invention.

BACKGROUND OF THE INVENTION

The present invention relates to mass spectrometry systems and in particular to a mass spectrometer providing improved quantification of the amounts of chromatographically separated materials, such as peptides and proteins, by parallel measurement of fluorescence.

SUMMARY OF THE INVENTION

Mass spectrometry (MS) has become a principal tool for identification of proteins and their post-translational modifications (PTMs), permitting routine identification of thousands of proteins and PTMs. Quantification of the amounts of the proteins and PTMs from these experiments, however, is required to further an understanding of the dynamics and subtleties of biological systems.

MS-based techniques for quantifying the amounts of the materials may employ gas-phase measurements of the proteins and PTMs measuring gas-phase ions most commonly generated by electrospray ionization (ESI) Yet highly variable peptide and protein ionization efficiencies often complicate quantification using gas-phase measurements. In addition to matrix effects (e.g., the effects of the material of a supporting matrix holding the proteins or PTMs for ionization), instrument platform-specific mass spectrometer biases may be introduced, making cross-platform quantification comparisons difficult.

In order to avoid these problems, solution-phase measurements may be employed, for example, providing separation of the proteins or PTMs by capillary electrophoresis or liquid chromatography (LC), followed by quantification (i.e. determination of the quantity) of selected amino acids in the proteins or PTMs by measured intrinsic fluorescence. Intrinsic fluorescence may be detected in selected amino acids of particular proteins of interest and when integrated with a known flow rate (and corrected by the expected amount of fluorescence for the protein) provides an indication of the amount of the protein. For example, separated phenylalanine, tyrosine, and tryptophan exhibit ultraviolet light-induced intrinsic fluorescence (UV-IF). Tryptophan-containing analytes have higher molar absorptivities relative to species containing phenylalanine or tyrosine providing higher quantum yields for fluorescence, and emit UV-IF at longer wavelengths. These chemical properties favor the measurement of UV-IF from tryptophan for the most sensitive native fluorescence assays.

SUMMARY OF THE INVENTION

The present invention provides improved quantification for mass spectrometry using an integrated electrospray emitter and fluorescence detector. Integration permits quantification on a single stream of analyte and the placement of the fluorescence detector immediately before the electrospray emitter provides improved correlation of between the measurements and for the reduction of chromatographic dead volume. A continuous capillary may be used to provide not only the electrospray emitter but also the liquid chromatography column allowing effective analysis of extremely small amounts of material at nanoliter flow rates and a significant reduction in dead volume which may cause a loss of chromatographic resolution and sensitivity.

Specifically, the present invention provides an electrospray emitter assembly for mass spectrometry having a conduit with a substantially continuous portion extending along a conduit axis and terminating at an orifice adapted to provide electrospray ionization for mass spectrometer. The continuous portion provides a transparent analysis region and a light source is positioned adjacent to the transparent section for projecting light into the transparent section to excite fluorescent material contained in the conduit. A light detector is positioned adjacent to the transparent section for receiving the light emitted by the fluorescent material contained in the conduit. A volume of a conduit between the orifice and the transparent section is less than 1 microliter.

It is thus a feature of at least one embodiment of the invention to provide simultaneous mass spectrometry and fluorescence analysis with improved correlation between these measurements.

The conduit is a glass capillary tube, and may, for example, have an internal diameter of less than 1000 µm.

It is thus a feature of at least one embodiment of the invention to provide for fluorescence quantification with extremely small volumes of sample material.

The electrospray emitter may include a filter position before the transparent analysis region for confinement of chromatographic packing material.

It is thus a feature of at least one embodiment of the invention to permit close proximity of the end of the LC column to the fluorescence analysis for reduced dead volume effects.

The filter may be a cast chemical frit.

It is thus a feature of at least one embodiment of the invention to provide a simple method of fabrication of filters within extremely small capillary tubes.

The electrospray emitter may include a bubble-reducing element positioned in the conduit after the filter.

It is thus a feature of at least one embodiment of the invention to reduce the formation of gas bubbles that may interfere with fluorescence measurement in extremely small sample sizes in which even small bubbles may displace a substantial proportion of the sample.

The liquid chromatography column may be positioned before the transparent analysis section to provide a separated analyte to the transparent analysis region, the liquid chromatography column having an internal diameter substantially equal to a diameter of the conduit.

It is thus a feature of at least one embodiment of the invention to provide a combination LC/MS system suitable for use with very small sample sizes.

The liquid chromatography column may be provided by a substantially continuous portion of the conduit extending away from the orifice beyond the transparent analysis region.

It is thus a feature of at least one embodiment of the invention to provide a simple and convenient single replaceable element for LC/MS experiments.

The electrospray emitter assembly may further include a ball lens adjacent to the transparent portion between the light source and the transparent portion.

It is thus a feature of at least one embodiment of the invention to provide a compact lens system that may work with extremely small capillary tubes ensuring focus internal to the tube while conforming to space limitations necessary to fit the optical system in the mass spectrometry system close to the electrospray emitter.

The light source may be an LED.

It is thus a feature of at least one embodiment of the invention to provide an illumination system that is both robust and inexpensive and may be positioned closely adjacent to the inlet of the magnetic spectrometry system.

The light detector may include a light filter selectively passing a frequency of light associated with the fluorescence.

It is thus a feature of at least one embodiment of the invention to provide a system that may be flexibly employed in a variety of different experiments.

The light source may project light along a first light axis substantially perpendicular to the conduit axis and the light detector may receive light along a second light axis substantially perpendicular to the first light axis and the conduit axis.

It is thus a feature of at least one embodiment of the invention to minimize background illumination from the light source.

These particular features and advantages may apply to only some embodiments falling within the claims and thus do not define the scope of the invention. The following description and figures illustrate a preferred embodiment of the invention Such an embodiment does not necessarily represent the full scope of the invention, however. Furthermore, some embodiments may include only parts of a preferred embodiment. Therefore, reference must be made to the claims for interpreting the scope of the invention.

DETAILED DESCRIPTION OF THE PREFERRED EMBODIMENT

Figure 1:
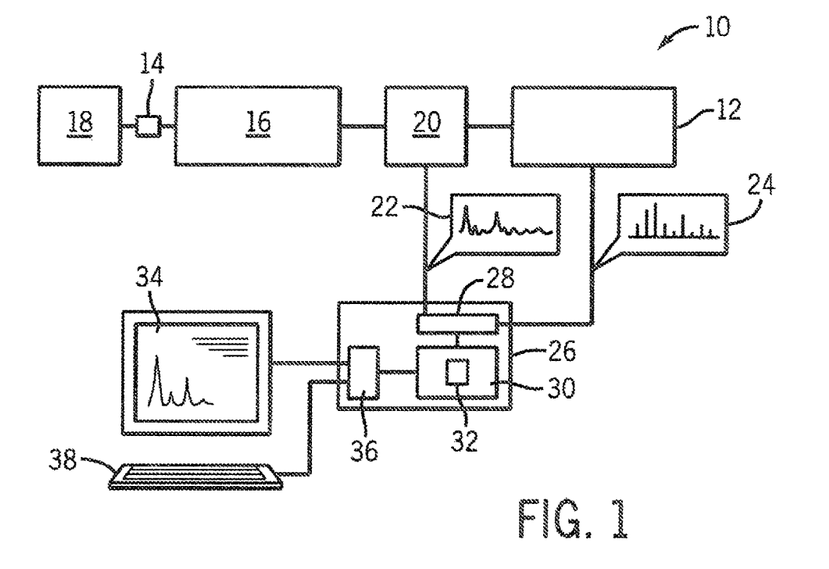
FIG. 1 is a block diagram of a mass spectrometer system incorporating the present invention.

Referring now to FIG. 1, a mass spectrometer system 10 of the present invention may provide a mass spectrometer (MS) 12, for example, being any of various types of mass spectrometers including; sector, time of flight, ion trap, oribitrap, and cyclotron type designs and others.

The mass spectrometer 12 may receive an analyte 14 for analysis as pumped through a liquid chromatography (LC) column 16 by a pumping mechanism 18 of a type known in the art. The pumping mechanism 18 may provide a known flow rate. Isolated fractions exiting the LC column 16 may be received by an intrinsic fluorescence (IF) detector 20 before passing to the mass spectrometer 12. The IF detector 20 may provide for fluorescence data 22 indicating fluorescence intensity of the analyte 14 as a function of time and the mass spectrometer 12 may provide for mass spectrometry data 24 (m/z) also as a function of time.

The fluorescence data 22 and mass spectrometry data 24 may be received by an electronic computer 26 at interface 28. Electronic computer 26 may include a processor 30 executing a stored program 32, to process the received fluorescence data 22 and mass spectrometry data 24, and may further provide an output (graphical or quantitative) on display screen 34 via interface 36. Interface 36 may also receive control data or input by the user through a keyboard 38 or the like.

Figure 2:
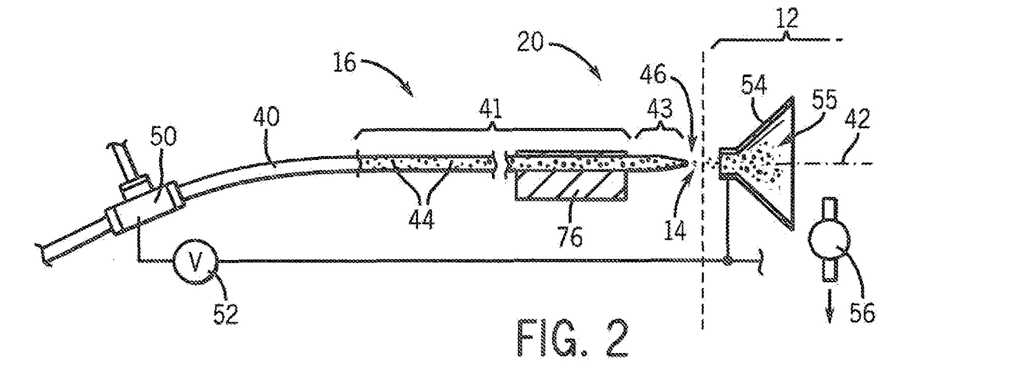
FIG. 2 is a fragmentary top plan view of a capillary providing a combination LC column, fluorescence detector region, and electrospray emitter for use in the mass spectrometer system of FIG. 1.

Referring now to FIG. 2, the LC column 16 and IF detector 20 may be implemented by different portions of a single continuous capillary 40 extending along an axis 42. The capillary 40 may be, for example, constructed of a generally transparent glassy material such as fused silica. The term "glass" as used herein is not intended to be limited to so-called soda-lime glass, but includes any similar material. The capillary 40 may have an inner diameter of less than 100 μm and typically less than 200 μm.

An end of the capillary 40, positionable adjacent to the mass spectrometer 12, is tapered to an orifice 46 of smaller diameter than the diameter of the capillary 40, and sized as is understood in the art to provide an electrospray emitter for the mass spectrometer 12.

Figure 6:
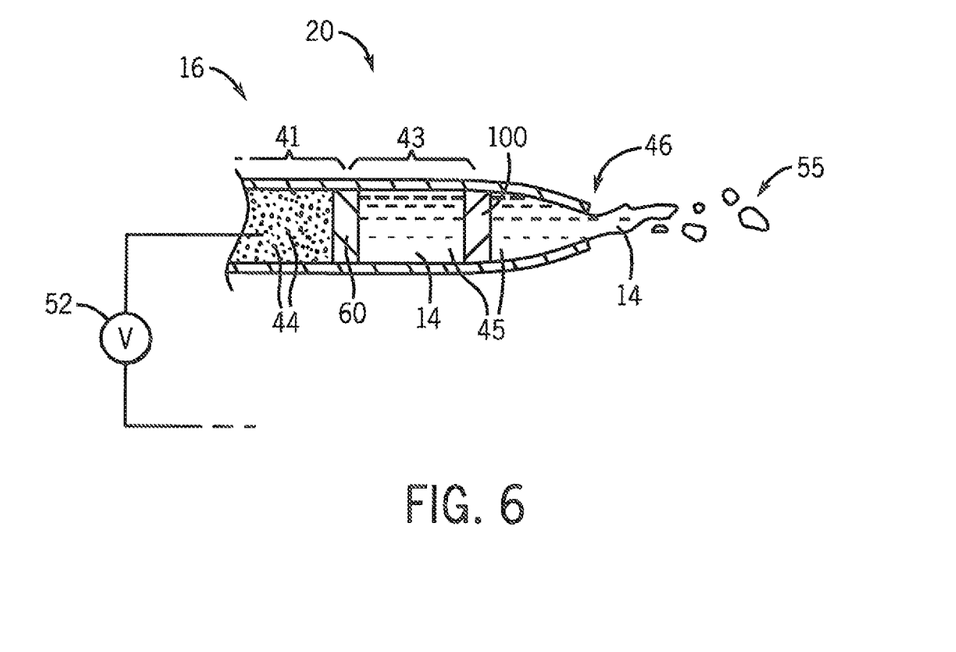
FIG. 6 is a cross-sectional view of an emitter of the capillary of FIG. 2 showing an optional multistage filter for reducing bubbles in the fluorescence measuring region.

Referring also to FIG. 6, a first portion 41 of the capillary 40 furthest from the orifice 46 may provide the LC column 16 and for this purpose may contain a chromatographic packing material 44 selected for the particular analysis and separation required as is understood in the art. This first portion 41 of the capillary 40 may be coated with a polymer to improve its resilience and thus may be substantially light blocking or translucent.

The first portion 41 of the capillary providing the LC column 16 may connect at its end closest to the orifice 46 to a second portion 43 of the capillary 40 associated with the IF detector 20. This second portion 43 of the capillary 40 provides transparent walls permitting the fluorescence analysis to be described. Ideally, the first portion 41 of the capillary providing the LC column 16 is separated from the orifice 46 by a small volume 45 including the second portion 43 of less than a microliter and preferably less than 300 nanoliters.

Referring still to FIGS. 2 and 6, an end of the capillary 40 removed from the orifice 46 may be attached to a metallic tee fitting 50 which may provide electrical communication to material within the capillary 40 and which may be connected to a voltage source 52 associated with a mass spectrometer 12. The voltage source 52, as is understood in art, provides an electrical bias between the analyte 14 exiting the orifice 46 and a receiving cone 54 of the mass spectrometer 12. In this regard, it will be understood that analyte 14 may be pumped through the capillary 40 toward the orifice 46 to eject from the orifice 46 and to be drawn into the receiving cone 54 of the mass spectrometer breaking into a fine spray 55 of droplets whose solvent evaporates to yield multiple isolated ionized molecules. Generally, the volume behind the receiving cone 54 will be at low pressure as provided by one or more vacuum pumps 56 also serving to guide material from the orifice 46 into the receiving cone 54.

Referring specifically to FIG. 6, the packing material 44 in first portion 41 of the capillary 40 and providing the LC column 16 may abut an internal filter 60 spanning the internal diameter of the capillary 40 and sized to block the passage of the packing material 44 toward the orifice 46. Filter 60 may be placed before the second portion 43 providing the IF detector 20 to prevent packing material from interfering with this detection process. The filter 60 may be constructed, for example, by heat-induced polymerization of a silicate solution introduced into the capillary and forming a cast chemical frit.

Figure 3:
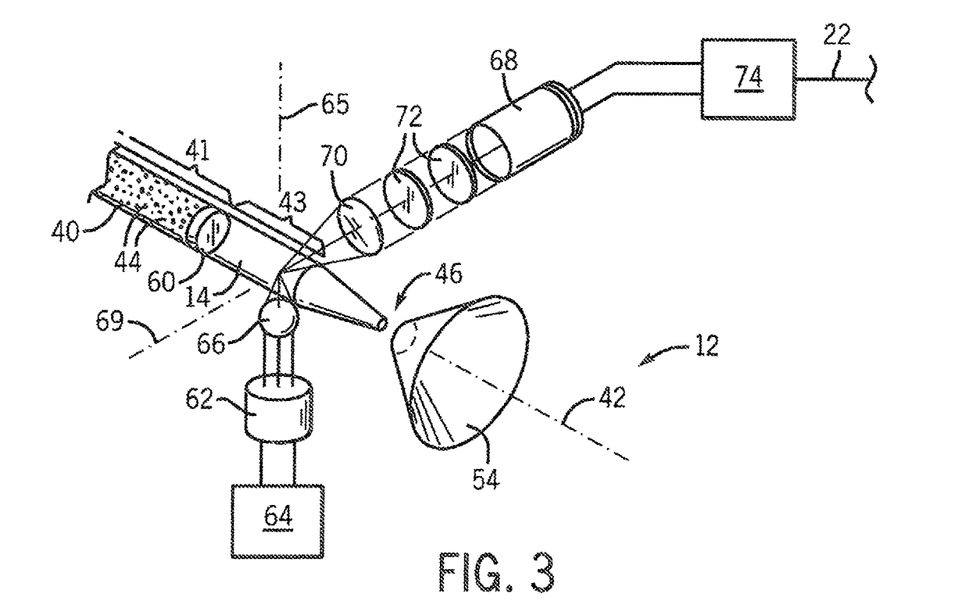
FIG. 3 is a simplified perspective view of an optical assembly for detecting fluorescence of material within the capillary of FIG. 2.

Referring now to FIG. 3 fluorescence may be detected in the second portion 43 by stimulating the analyte 14 within the second portion 43 by light from a light source 62, for example an LED, provided with power from a power supply 64. The light from the light source 62 may be projected upward vertically along an axis 65 perpendicular to the axis 42 and focused into the center of the capillary 40 in the second portion 43 by a ball lens 66. Fluorescence excited in the analyte 14 in the second portion 43 by this illumination may be detected by a detector 68, for example a photomultiplier tube, receiving light through a focusing lens 70 along an axis 69 perpendicular to the axes 65 and 42 so as to reduce direct transmission of light from the light source 62 to the detector 68. One or more filters 72 may be used to eliminate light outside of the frequency of the desired detected fluorescence. The detector 68 may provide a signal to amplifier 74 which produces the fluorescence data 22.

Figures 4, 5:
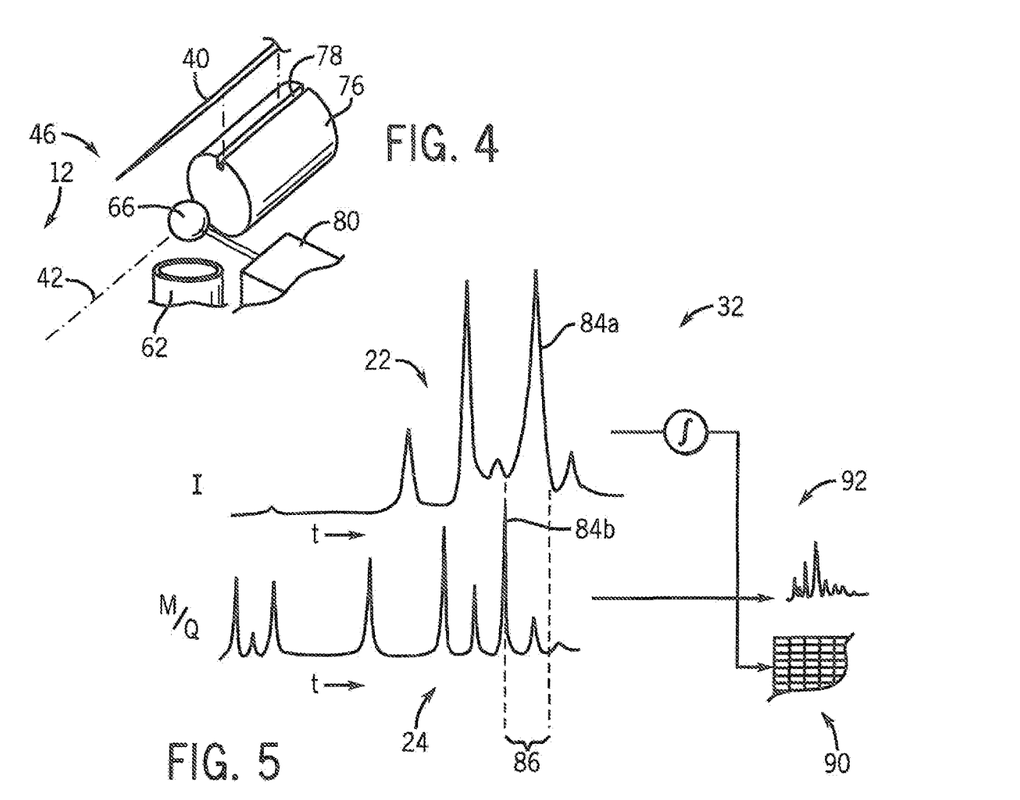
FIG. 4 is a fragmentary detail of support structures for the capillary of FIG. 2 permitting simple replacement of that capillary.
FIG. 5 is a diagram showing the processing of data collected from the mass spectrometer and the fluorescence detector to provide a combined readout and quantification of mass spectrometer identified fractions.

Referring now to FIG. 4, the capillary 40 may be supported on a support structure 76, for example a metallic rod, having a groove 78 sized to receive the capillary in alignment with axes 42 at a predetermined height with respect to the mass spectrometer 12. The capillary 40 may be held within the groove 78 by means of releasable ties or adhesive tape or the like (not shown). The support structure 76 may be fixed to the structure of the mass spectrometer 12 so that the capillary 40, when replaced, may be repeatedly located with respect to the mass spectrometer 12. In this way, rapid change of capillaries 40 is possible. The ball lens 66 which desirably touches or is closely proximate to the capillary 40 may be supported on a movable stage 80 so that it may be adjusted as necessary.

Referring now to FIG. 5, the fluorescence data 22 and mass spectrometry data 24 may be operated on by the program 32 (shown in FIG. 1) to provide alignment of this data so that peaks in each data set for similar fractions of the analyte 14 are aligned. This alignment compensates for the transit time between the analysis zone of the second portion 43 of the capillary (for example shown in FIG. 2) and the time taken for the analyte 14 to move out of the orifice 46 and the resulting electrospray 55 to pass through and be detected by the mass spectrometer 12. The alignment may identify a first and second peak 84a and 84b in the fluorescence data 22 and mass spectrometry data 24 respectively, for example, with operator guidance, to identify and offset 86 in time and shift one or both of the fluorescence data 22 and mass spectrometry data 24 to eliminate that offset. In this way, close correlation between the fluorescence data 22 and mass spectrometry data 24 may be made.

The fluorescence data 22 may be integrated, for example, at certain time ranges around each peak in the mass spectrometry data 24, as a function of known or measured flow rate, so as to produce absolute quantification values for each peak which may be provided in a table output 90 along with identification of the materials associated with each peak of the mass spectrometry data 24 according to techniques known in the art. Alternatively the data may be displayed graphically in a graph 92, for example, with plots of the fluorescence data 22 and mass spectrometry data 24 superimposed with different colors or the like. In addition the fluorescence data 22 may be deconvolved using kernels that may be empirically linked to the particular capillaries 40 and the experiment being conducted. The small dead volume will allow improved kernel definition.

Referring now to FIG. 6, the filter 60 positioned at the beginning of the second portion 43 may be followed by a second filter 100 to preserve a back pressure that may help reduce bubbles in the second portion 43 such as may interfere with the fluorescence measurement.

Example I

Chemicals and Reagents

Tryptophan-containing peptides LPRSAYWHHITG, WWGKKYRASKLGLAR, FLWGPRALV, and YGGFLR-RIRPKLKWDNQ were purchased from AnaSpec (Fremont, Calif.) in >95% purity and were reconstituted in 0.2% formic acid for immediate use. AQUA QuantPro peptides were purchased from Thermo Scientific (Bremen, Germany) in solution form with manufacturer-validated concentrations within 25% of the stated amount. High-purity formic acid and acetonitrile were purchased from Fisher Scientific (Waltham, Mass.). A NANOpure Diamond deionization system (Barnstead International; Dubuque, Iowa) was used to generate 18.2 MΩ water used in LC analyses. All additional standard proteins and reagents were obtained from Sigma Aldrich (Milwaukee, Wis.) unless otherwise specified.

Fluorescence Excitation and Detection Device.

The design of the fluorescence excitation and detection system was modeled after that of Sluszny and co-workers and adapted for use with nanoLC. See Sluszny, C.; He, Y.; Yeung, E. S. Electrophoresis 2005, 26, 4197-1 4203.2 hereby incorporated by reference. A capillary LC column with detection cell and integrated electrospray emitter was mounted to a bread-board by sliding it through a PEEK tubing sleeve secured into a locating groove on a fixed metal rod. The last 5-10 min of the capillary containing the detection cell extended out over an AlInGaN UV-LED (UVTOP-280-TO39BL, Sensor Electronic Technology, Columbia, S.C.). The capillary detection cell was placed 11 mm above the center of the LED's integrated ball lens. The LED was placed inside an aluminum sleeve supporting a bandpass interference filter (Semrock, Rochester, N.Y.) with a center wavelength of 280 μm and a bandwidth of 20 nm. A second fused silica ball lens with a diameter of 4 mm (ISP Optics, Irvington, N.Y.) was placed between the LED and the capillary. This lens was mounted on a 3-D translation stage and positioned such that the capillary was nearly resting upon the lens. UV-IF was collected at 90 degrees relative to the excitation light using a fused silica plano-convex lens with a diameter of 0.5 in. and focal length of 19 mm (Newport, Irvine, Calif.). This lens was also mounted on a 3-D translation stage. UV-IF was passed through an aperture with a diameter of 0.5 in. positioned 95 mm beyond the collection lens. This aperture was at the entrance of a black Delrin tube (1 in i.d., 75 mm long) that housed a long-pass colored-glass filter with a cut-on wavelength of 324 nm (Newport) followed by a bandpass interference filter with a center wavelength of 357 nm and a bandwidth of 44 nm (Semrock). The LED was powered by an LED power supply (LED PS, SandHouse Design, FL) operated at 5-20 mA. Light detection was performed by an R928 photomultiplier tube (Hamamatsu Photonics, Hamamatsu, Japan).

The breadboard supporting the entire system was mounted on a 3-D translation stage to allow fine positioning of the electrospray emitter at the MS inlet. Signal from the photomultiplier was passed through a home-built current-to-voltage converter. The voltage was sampled using a PCI-6035E card (National Instruments, Austin, Tex.) within a personal computer running Windows XP. Signal processing was done using a program written in Lab VIEW 8.5 1 (National Instruments, Austin, Tex.). The signal was sampled at a rate of 100 kHz, and $10^4$ samples were averaged to produce one recorded data point, resulting in the generation of 10 data points per second.

LC Column Fabrication.

Microcapillary columns containing an integrated detection cell and ESI emitter were fabricated in-house. Fused silica tubing (360 µm o.d.×200 µm i.d.) was used to prepare analytical columns slurry-packed to 15 cm in length with 3.5 µm, 130 Å particles of XBridge reversed-phase material (Waters Corp., Milford, Mass.) for peptide separations and Magic C18 AQ, 5 µm, 300 Å particles (Michrom Bioresources Inc., Auburn, Calif.) for intact protein separations. Chemical frits were cast by heat-induced polymerization of a silicate solution using a 125 degree C. soldering iron as described in Ficarro, S. B.; Zhang, Y.; Lu, Y.; Moghimi, A. R.; Askenazi, M.; 490 Hyatt, E.; Smith, E. D. Boyer, L.; Schlaeger, T. M.; Luckey, C. J.; Marto, 491 J. A. Anal. Chem, 2009, 81, 3440-3447, hereby incorporated by reference.

Integrated electrospray emitters were fabricated using a model P-2000 laser puller (Sutter Instrument Co., Novarto, Calif.) incorporating a 7-10 mm detection window between the chemical frit and electrospray emitter. Precolumns were constructed from 360 µm o.d.×200 µm i.d. fused silica with a cast chemical fit and slurry-packed with 8-10 cm of the same reversed-phase material used for either peptide or protein separations.

LC-MS/MS.

Gradient chromatographic elution was per-8 formed using a nanoACQUITY Ultra Performance LC system (Waters Corp.) at 500-1000 nL min analytical flow rates. An LTQ Orbitrap Velos enabled for ETD (Thermo Scientific, Bremen, Germany) was used for all MS and tandem MS (MS/2 MS) analyses. All MS selected ion chromatograms were generated from Orbitrap MS1 scans.

Fluorescence Detector Design and Characterization

Three of the standard 20 amino acids found in proteins are fluorescent: phenylalanine, tyrosine, and tryptophan. Tryptophan is the most sensitive of the three by a substantial factor, due to both a larger molar absorptivity and a greater quantum yield for fluorescence. Its fluorescence emission occurs at a longer wavelength than that of either phenylalanine or tyrosine, permitting optical discrimination.

Tryptophan is also a rare amino acid occurring infrequently in the proteomes of commonly studied organisms. Tryptophan represents 1.1% of the amino acids in the yeast (*Saccharomyces cerevisiae*) proteome. This scarcity is an advantage in the present study, as it means that fewer peptides or proteins will exhibit a fluorescence signal, reducing the requirements for their separation prior to fluorescence determinations (effectively reducing sample complexity). Yet, greater than 86% of yeast proteins contain tryptophan and 77% will produce a tryptophan-containing tryptic peptide, permitting the majority of proteins in this model organism to be interrogated.

On the basis of these considerations, we chose tryptophan as our target for online determination of peptide or protein concentration. We utilized a combination of emission filters that maximized the UV-IF signal-to-noise of tryptophan while minimizing the signal collected from tyrosine and phenylalanine. We selected a 280 nm UV-LED over a UV laser for its ease of implementation, low cost, and compact size. Initial experiments used a 12-V marine battery and home-built circuit to operate the UV-LED between 15 and 30 mA. Subsequent experiments used a power supply designed to operate the UV-5 LED at a constant current. The power supply provided more consistent LED output and increased LED lifetimes by ~25%. The average LED lifetime was 250 h while interfaced the mass spectrometer. NanoLC separations are commonly performed in packed fused silica capillaries with 360 µm outer diameters and 50-200 µm inner diameters. To reduce chromatographic band broadening, we integrated the detection cell into the fused silica separation column, which was terminated by the electrospray emitter. This design eliminated the need for bulky unions at the column, detection cell, and emitter junctions and allowed for routine LC backpressures exceeding 4000 psi. The choice of capillary inner and outer diameters had a significant impact on fluorescence signal We ultimately selected the 360 µm o.d.×200 µm i.d. capillary as a compromise between signal intensity, capillary strength, and ability to use standard 360 µm o.d. nanoLC fittings.

Effects of pH and Solvent on UV-IF.

UV-IF of indole-containing compounds, tryptophan, and tryptophan-containing peptides and proteins is modulated by local environment factors, including pH, solvent polarity, temperature, and structure. We examined the effects of solvent polarity and pH relevant to low-pH reversed-phase LC-MS separations. Tryptophan-containing peptides were dissolved in 0.2% formic acid with increasing percentages of acetonitrile, approximating a chromatographic gradient. Each peptide solution was infused through an unpacked fused-silica analytical column, and UV-IF was measured online using the fluorescence detector described above. For each 10% increase in acetonitrile concentration up to 40%, we saw a 4-10% increase in peptide UV-IF signal. A majority of tryptic peptides will elute from a C18 column in this 10-40% acetonitrile range. The trend begins to diminish at higher percentages of acetonitrile. We examined the effects of mobile-phase pH on UV-IF by infusing peptide solutions in 0.2% formic acid titrated with ammonium hydroxide to the desired pH. The UV-IF signal for three of the four peptides increased modestly with increasing pH (up to 4), at which point they began to level off. Interestingly, the UV-IF signal for the peptide containing tyrosine adjacent to tryptophan continued to increase across the tested range, although again the effect is small. The effects of both pH and solvent composition are relatively modest in magnitude, suggesting that these factors do not substantially compromise the utility of the UV-IF detection.

Peptide and Protein Digest LC Analysis.

To assess fluorescence detector performance during data-dependent LC-MS/MS analyses, we analyzed an equimolar (25%) mixture of 15 high-purity AQUA (absolute quantification) peptides. These particular AQUA peptides Were chosen, in part, for their ability to yield a strong and consistent positive ion ESI response and, thus, this set of 15 is not likely to be representative of all peptides in a proteome. Importantly, the signal intensity obtained from each of the single tryptophan peptides not containing tyrosine was similar within a factor of roughly 2. The peptide WPGYLNGGR, containing both a tryptophan and tyrosine residue, produced a lower intensity signal relative to the other single tryptophan-containing peptides. It has been reported that intrinsic fluorescence can be affected by both peptide/protein sequence and conformation and particularly by the presence of aromatic and ionizable residues. However, in this particular case, we suspect that a low concentration of the peptide is the main factor responsible for the lower signal of WPGYLNGGR since its normalized UV-IF intensity was in good agreement with its normalized MS intensity. This interpretation is supported by the observation that the signal intensity from the peptide NSWGTDWGEK, containing two nonadjacent tryptophan residues that are sufficiently distanced to minimize intramolecular fluorescence quenching, was roughly 2-fold greater than that of the other single tryptophan-containing peptides. As expected, no UV-IF signal was detected for peptides lacking tryptophan or tyrosine residues. These results indicate the utility of using UV-IF for obtaining an orthogonal measure of peptide concentration during an LC-MS/MS analysis, independent of the vagaries of peptide ionization efficiency. To evaluate the approach on a more biologically relevant sample, we digested commercially available proteins containing varying numbers of tryptophan residues and subjected them to online LC-MS/MS and UV-IF detection. Ribonuclease (zero Trp.) did not yield an appreciable peptide UV-IF response. Myoglobin (two Trp.) produced two distinct UV-IF peaks. The major peak was produced by a peptide containing two nonadjacent tryptophan residues. The minor peak was produced by a peptide containing both tyrosine and phenylalanine. Transferrin (eight Trp) produced six major peaks containing tryptophan and more than a dozen low-level peaks. Low-level UV-IF peaks corresponded to tryptophan-containing missed-cleavage peptides, peptides containing tryptophan and oxidized methionine, tyrosine-containing peptides, or peptides that could not be unambiguously identified. The analysis of transferrin revealed complications when trying to correlate UV-IF, MS, and database outputs in an efficient manner. UV-IF peak correlation to identified peptides from database outputs based on the retention time or spectrum number was often insufficient to confidently match peptide sequences to UV-IF peaks. Several tryptophan-containing peptides and UV-IF peaks often found in the same retention-time window complicated peak-sequence assignment. We achieved the most confident assignment of UV-IF peaks to peptide sequences by comparing selected ion chromatograms (SIC) of identified peptides to UV-IF peaks. The combination of SIC peak shape, especially peak width, and retention time was often helpful in the sequence assignment process when multiple tryptophan-containing peptides were identified over a small retention time window.

To facilitate the process of comparing peptide sequences with SICs and UV-IF peaks, we developed the software (FluorAid) that allows the user to select a peptide identified from database searching and automatically produces an SIC for the selected peptide. A UV-IF chromatogram is produced on the same graph centered on the retention time of the identified peptide with a user-defined window. The user can quickly scroll through the list of identified peptides to determine the best match. We have found this simple software tool to be of great help for analysis of UV-IF and MS results. The software is open source and freely available at http://www.chem.wisc.edu/~coon/software.php.

Peptide Linear Dynamic Range and Quantification.

We evaluated the linear dynamic range of detection for UV-IF peptide analysis using peak area integration of three tryptophan-containing peptides identified from a tryptic digest of lysozyme (six Trp). The UV-IF linear dynamic range was comparable to that of MS ion current in the range of 25 fmol to 8 pmol. UV-IF $r^2$ values exceeded 0.99, with similar responses for all three peptides. The UV-IF response of the peptide WWCNDGR, containing two adjacent tryptophan residues, was similar to those containing a single tryptophan, suggesting internal fluorescence quenching. Similar linear dynamic ranges were generated from other single protein digests. In nearly all cases, MS SICs provided lower limits of detection (~5 fmol) by a factor of 3-5. However, when peptides contained multiple nonadjacent tryptophan residues, UV-IF produced limits of detection approaching subfemtomolar levels. To further assess the use of UV-IF for peptide/protein quantification, an estimated equimolar mixture of conalbumin, transferrin, serum albumin, enolase, and aldolase containing 10, 8, 5, 4, and 3 tryptophan residues, respectively, was digested and analyzed in triplicate. As expected, due to the relatively low frequency of tryptophan-containing peptides, the UV-IF chromatogram is considerably less complex than the MS base-peak chromatogram. We compared peak area estimates for resolved or partially resolved tryptophan-containing peptides filtered to a 1% false discovery rate (FDR) to peak areas generated from MS SICs of selected peptides. Peptides identified as missed-cleavage products or containing oxidized methionine residues were grouped for quantification. Response was normalized to the highest responding peptide for UV-IF or MS, respectively.

Conalbumin, transferrin, and enolase produced multiple tryptophan-containing peptides. Serum albumin and aldolase each produced one confidently identified peptide and were excluded for quantification. Upon summation and normalization of peak areas from the tryptophan-containing peptides, the UV-IF results yield relative abundances of the three proteins of 0.9:1.0:0.8, while the MS results yield a ratio of 0.7:1.0:0.5. Thus, a somewhat improved measure of protein relative abundance was obtained from the UV-IF data than from the MS data, along with improved run-to-run reproducibility. There is greater variability in the MS peak areas than in the UV-IF peak areas (the average standard errors of the mean for the two sets of data are 4.2% for the UV-IF, versus 7.8% for the MS). There was little correlation between the two responses (r=0.36) for the 31 tryptophan-containing peptides identified from this sample. Yet, both methods produced comparable quantification at the protein level. This suggests these solution- and gas-phase peptide measurements are highly orthogonal, providing complementary information about vastly different peptide attributes, i.e., intrinsic fluorescence and ionization/transmission efficiencies. These data demonstrate that UV-IF can be used to estimate protein abundance from simple protein digests using peptides identified from parallel MS/MS analyses.

Application to Top-Down LC-MS.

We investigated the use of intrinsic fluorescence for the interrogation of intact proteins using top-down LC-MS. Estimated equimolar quantities (~11 pmol each) of transferrin, R-casein, and ribonuclease were individually analyzed with composite UV-IF and MS SICs. Protein relative responses for each detector were determined by peak area integration. MS protein response scaled with protein molecular weight: ribonuclease (13.7 kDa) produced the greatest response, followed by R-casein (24.5 kDa) and transferrin (77 kDa). UV-IF response increased with the number of tryptophan residues. Ribonuclease (zero Trp) produced very little UV-IF, whereas R-casein (two Trp) and transferrin (eight Tip) produced increasingly greater responses. The peak area of transferrin was ~4 times larger than α-casein and very closely scaled with the number of tryptophan residues in each protein in agreement with previously reported observations. Monitoring UV-IF during top-down analysis may be a promising application for the detection, identification, and quantification of intact proteins. High-quality top-down spectra often require significant spectral averaging, leading to very long MS/MS duty cycles and few measured points across a peak. UV-IF does not suffer the same duty cycle penalties and may offer a label-free approach for intact protein quantification, offering substantially lower limits of detection for both large and tryptophan-rich proteins. Moreover. UV-IF may be particularly advantageous for detection and quantification of larger (>30 kDa) or poorly ionizing proteins for which the correlation between MS signal and protein abundance is low.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more controllers or processors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. An electrospray emitter for mass spectrometry and fluorescent spectroscopy comprising:
   a conduit having a substantially continuous portion extending along a conduit axis and terminating at an orifice adapted to provide an electrospray ionization for a mass spectrometer;
   chromatographic packing material positioned within a chromatography portion of the continuous portion;
   a first filter fitting within the conduit and sized to block the chromatographic packing material;
   a second filter fitting within the conduit downstream from the first filter and sized to preserve a liquid pressure within the conduit; and
   a transparent analysis region positioned within the continuous portion between the first filter and the second filter adapted for fluorescent spectroscopy measurement;
   wherein a volume of a conduit between the orifice and the chromatography portion is less than 1 microliter.

2. The electrospray emitter assembly of claim 1 wherein the conduit is a glass capillary tube.

3. The electrospray emitter assembly of claim 1 wherein an internal diameter of the conduit is less than 1000 μm.

4. The electrospray emitter assembly of claim 1 wherein the first filter is a cast chemical frit.

5. An electrospray emitter for mass spectrometry and fluorescent spectroscopy comprising:
   a conduit having a substantially continuous portion extending along a conduit axis and terminating at an orifice adapted to provide an electrospray ionization for a mass spectrometer;
   chromatographic packing material positioned within a chromatography portion of the continuous portion;
   a filter fitting within the conduit and sized to block the chromatographic packing material;
   a bubble reducing element positioned in the conduit downstream from the filter; and
   a transparent analysis region positioned within the continuous portion between the first fitting and the bubble reducing element adapted for fluorescent spectroscopy measurement;
   wherein a volume of a conduit between the orifice and the chromatography portion is less than 1 microliter.

6. The electrospray emitter assembly of claim 5 wherein the conduit is a glass capillary tube.

7. The electrospray emitter assembly of claim 5 wherein an internal diameter of the conduit is less than 1000 μm.

8. The electrospray emitter assembly of claim 5 wherein the first filter is a cast chemical frit.

* * * * *